(12) United States Patent
Legrand et al.

(10) Patent No.: US 8,101,209 B2
(45) Date of Patent: *Jan. 24, 2012

(54) MICROPARTICULATE ORAL GALENICAL FORM FOR THE DELAYED AND CONTROLLED RELEASE OF PHARMACEUTICAL ACTIVE PRINCIPLES

(75) Inventors: Valérie Legrand, Lyons (FR); Catherine Castan, Orlienas (FR); Rémi Meyrueix, Lyons (FR); Gérard Soula, Meyzieu (FR)

(73) Assignee: Flamel Technologies (FR)

( * ) Notice: Subject to any disclaimer, the term of this patent is extended or adjusted under 35 U.S.C. 154(b) by 1068 days.

This patent is subject to a terminal disclaimer.

(21) Appl. No.: 10/826,690

(22) Filed: Apr. 19, 2004

(65) Prior Publication Data

US 2004/0234601 A1    Nov. 25, 2004

Related U.S. Application Data

(63) Continuation-in-part of application No. 10/492,129, filed as application No. PCT/FR02/03443 on Oct. 9, 2002.

(30) Foreign Application Priority Data

Oct. 9, 2001 (FR) ..................................... 01 12999

(51) Int. Cl.
   *A61K 9/16* (2006.01)
   *A61K 9/50* (2006.01)

(52) U.S. Cl. ........ 424/498; 424/489; 424/490; 424/494; 424/497; 514/951; 514/963; 514/965

(58) Field of Classification Search .................. 424/469, 424/458, 459, 461, 462, 489, 490, 497, 498, 424/501, 494; 514/951, 963, 965
See application file for complete search history.

(56) References Cited

U.S. PATENT DOCUMENTS

| | | |
|---|---|---|
| 3,845,770 A | 11/1974 | Theeuwes et al. |
| 3,864,483 A | 2/1975 | Stein et al. |
| 3,892,769 A | 7/1975 | Shen et al. |
| 3,914,414 A | 10/1975 | Stein et al. |
| 3,914,415 A | 10/1975 | Stein et al. |
| 3,927,216 A | 12/1975 | Witkowski et al. |
| 3,966,917 A | 6/1976 | Prasad et al. |
| 3,980,766 A | 9/1976 | Shaw et al. |
| 4,029,884 A | 6/1977 | Stein et al. |
| 4,036,227 A | 7/1977 | Zaffaroni et al. |
| 4,070,494 A | 1/1978 | Hoffmeister et al. |
| 4,077,407 A | 3/1978 | Theeuwes et al. |
| 4,111,203 A | 9/1978 | Theeuwes |
| 4,218,433 A | 8/1980 | Kooichi et al. |
| 4,308,251 A | 12/1981 | Dunn et al. |
| 4,321,253 A | 3/1982 | Beatty |
| 4,434,153 A | 2/1984 | Urquhart et al. |
| 4,454,309 A | 6/1984 | Gould et al. |
| 4,461,759 A | 7/1984 | Dunn |
| 4,486,471 A | 12/1984 | Samejima et al. |
| 4,503,067 A | 3/1985 | Wiedemann et al. |
| 4,519,801 A | 5/1985 | Edgren |
| 4,553,973 A | 11/1985 | Edgren |
| 4,572,912 A | 2/1986 | Yoshioka et al. |
| 4,609,374 A | 9/1986 | Ayer |
| 4,610,686 A | 9/1986 | Ayer et al. |
| 4,612,008 A | 9/1986 | Wong et al. |
| 4,624,847 A | 11/1986 | Ayer et al. |
| 4,639,436 A | 1/1987 | Junge et al. |
| 4,687,660 A | 8/1987 | Baker et al. |
| 4,693,896 A | 9/1987 | Wheatley et al. |
| 4,717,569 A | 1/1988 | Harrison et al. |

(Continued)

FOREIGN PATENT DOCUMENTS

CA    2068366    11/1992

(Continued)

OTHER PUBLICATIONS

Sigma-Aldrich Particle Size Conversion, 2010, http://www.sigmaaldrich.com/chemistry/stockroom-reagents/learning-center/technical-library/particle-size-conversion.html.*

(Continued)

*Primary Examiner* — Michael G Hartley
*Assistant Examiner* — Leah Schlientz
(74) *Attorney, Agent, or Firm* — Patton Boggs LLP

(57) ABSTRACT

The invention relates to a microparticulate system for the delayed and controlled release of active principles (AP) whose absorption window in vivo is essentially limited to the upper parts of the gastrointestinal tract, this system being intended for oral administration. The object of the invention is to provide a system ensuring that the AP is released with certainty by means of a dual mechanism of "time-dependent" and "pH-dependent" release. To achieve this object, the invention proposes a multimicrocapsular oral galenical form which is designed so as to guarantee therapeutic efficacy, and in which the release of the AP is governed by a dual release triggering mechanism that is "time-triggering" and "pH-triggering". This system comprises of microcapsules (200 to 600 μm) comprising a core of AP coated with a film (maximum 40% by weight) comprising a hydrophilic polymer A (Eudragit® L) and a hydrophobic compound B (vegetable wax, melting point=40-90° C.), B/A being between 0.2 and 1.5. These microcapsules have a dissolution behavior in vitro such that, at a constant pH of 1.4, a latency phase of between 1 and 5 hours is observed, followed by a release of the AP, and such that the change from pH 1.4 to pH 6.8 results in a release of the AP without a latency period in vitro.

17 Claims, 2 Drawing Sheets

U.S. PATENT DOCUMENTS

| | | | |
|---|---|---|---|
| 4,728,512 A | 3/1988 | Mehta et al. | |
| 4,748,023 A | 5/1988 | Tamas et al. | |
| 4,758,579 A | 7/1988 | Kohl et al. | |
| 4,777,049 A | 10/1988 | Magruder et al. | |
| 4,782,043 A | 11/1988 | Boger et al. | |
| 4,792,448 A | 12/1988 | Ranade | |
| 4,814,182 A | 3/1989 | Graham et al. | |
| 4,814,183 A | 3/1989 | Zentner | |
| 4,816,262 A | 3/1989 | McMullen | |
| 4,832,958 A | 5/1989 | Baudier et al. | |
| 4,833,905 A | 5/1989 | Hill | |
| 4,844,905 A | 7/1989 | Ichikawa et al. | |
| 4,861,599 A | 8/1989 | Springolo et al. | |
| 4,892,738 A | 1/1990 | Takagishi et al. | |
| 4,894,240 A | 1/1990 | Geoghegan et al. | |
| 4,902,513 A | 2/1990 | Carvais | |
| 4,904,769 A | 2/1990 | Rauenbusch | |
| 4,952,402 A | 8/1990 | Sparks et al. | |
| 4,985,454 A | 1/1991 | Leinert | |
| 4,999,189 A | 3/1991 | Kogan et al. | |
| 5,004,614 A | 4/1991 | Staniforth | |
| 5,028,434 A | 7/1991 | Barclay et al. | |
| 5,043,167 A | 8/1991 | Rotini et al. | |
| 5,045,321 A | 9/1991 | Makino et al. | |
| 5,051,262 A | 9/1991 | Panoz et al. | |
| 5,071,868 A | 12/1991 | Leinert | |
| 5,084,278 A | 1/1992 | Mehta | |
| 5,091,485 A | 2/1992 | Noireaux et al. | |
| 5,158,636 A | 10/1992 | Groitzsch et al. | |
| 5,186,930 A | 2/1993 | Kogan et al. | |
| 5,206,030 A | 4/1993 | Wheatley et al. | |
| 5,248,516 A | 9/1993 | Wheatley et al. | |
| 5,268,182 A | 12/1993 | Brinker et al. | |
| 5,286,497 A | 2/1994 | Hendrickson et al. | |
| 5,308,862 A | 5/1994 | Ohlstein | |
| 5,393,772 A | 2/1995 | Yue et al. | |
| 5,405,619 A * | 4/1995 | Santus et al. | 424/490 |
| 5,405,863 A | 4/1995 | Barone et al. | |
| 5,409,709 A | 4/1995 | Ozawa et al. | |
| 5,409,711 A | 4/1995 | Mapelli et al. | |
| 5,431,922 A | 7/1995 | Nicklasson | |
| 5,445,829 A | 8/1995 | Paradissis et al. | |
| 5,453,436 A | 9/1995 | Ohlstein | |
| 5,464,632 A | 11/1995 | Cousin et al. | |
| 5,472,704 A | 12/1995 | Santus et al. | |
| 5,571,533 A | 11/1996 | Santus et al. | |
| 5,594,016 A | 1/1997 | Ueno et al. | |
| 5,603,957 A | 2/1997 | Burguiere et al. | |
| 5,643,915 A | 7/1997 | Andrulis, Jr. et al. | |
| 5,643,939 A | 7/1997 | Ohlstein | |
| 5,651,990 A | 7/1997 | Takada et al. | |
| 5,656,295 A | 8/1997 | Oshlack et al. | |
| 5,674,529 A | 10/1997 | Marder et al. | |
| 5,760,069 A | 6/1998 | Lukas-Laskey et al. | |
| 5,780,055 A | 7/1998 | Habib et al. | |
| 5,783,215 A | 7/1998 | Arwidsson et al. | |
| 5,804,573 A | 9/1998 | Silver | |
| 5,846,566 A | 12/1998 | Burguiere et al. | |
| 5,858,398 A | 1/1999 | Cho | |
| 5,902,821 A | 5/1999 | Lukas-Laskey et al. | |
| 5,922,769 A | 7/1999 | Barelli et al. | |
| 5,945,123 A | 8/1999 | Hermelin | |
| 5,955,106 A | 9/1999 | Moeckel et al. | |
| 6,019,735 A | 2/2000 | Kensey et al. | |
| 6,022,562 A | 2/2000 | Autant et al. | |
| 6,024,982 A | 2/2000 | Oshlack et al. | |
| 6,033,687 A | 3/2000 | Heinicke et al. | |
| 6,034,091 A * | 3/2000 | Dante | 514/282 |
| 6,043,252 A | 3/2000 | Bombrun | |
| 6,056,968 A | 5/2000 | Gilbert et al. | |
| 6,068,859 A | 5/2000 | Curatolo et al. | |
| 6,077,544 A | 6/2000 | Debregeas et al. | |
| 6,096,341 A * | 8/2000 | Seth | 424/482 |
| 6,096,777 A | 8/2000 | Feuerstein et al. | |
| 6,099,862 A | 8/2000 | Chen et al. | |
| 6,184,220 B1 | 2/2001 | Turck et al. | |
| 6,214,854 B1 | 4/2001 | Wang et al. | |
| 6,221,377 B1 | 4/2001 | Meyer | |
| 6,224,909 B1 | 5/2001 | Opitz et al. | |
| 6,228,398 B1 | 5/2001 | Devane et al. | |
| 6,248,359 B1 | 6/2001 | Faour | |
| 6,264,983 B1 | 7/2001 | Upadhyay | |
| 6,274,173 B1 | 8/2001 | Sachs et al. | |
| 6,303,146 B1 | 10/2001 | Bonhomme et al. | |
| 6,309,663 B1 | 10/2001 | Patel et al. | |
| 6,309,668 B1 | 10/2001 | Bastin et al. | |
| 6,322,525 B1 | 11/2001 | Kensey et al. | |
| 6,358,990 B1 | 3/2002 | Howlett et al. | |
| 6,379,706 B2 | 4/2002 | Opitz et al. | |
| 6,395,300 B1 | 5/2002 | Straub et al. | |
| 6,403,579 B1 | 6/2002 | Heller | |
| 6,419,960 B1 | 7/2002 | Krishnamurthy et al. | |
| 6,428,488 B1 | 8/2002 | Kensey et al. | |
| 6,428,809 B1 | 8/2002 | Abrams et al. | |
| 6,432,989 B1 | 8/2002 | Chen | |
| 6,462,047 B1 | 10/2002 | Bombrun et al. | |
| 6,472,373 B1 | 10/2002 | Albrecht | |
| 6,475,521 B1 | 11/2002 | Timmins et al. | |
| 6,484,565 B2 | 11/2002 | Shin et al. | |
| 6,491,949 B2 | 12/2002 | Faour et al. | |
| 6,495,154 B1 | 12/2002 | Tam et al. | |
| 6,515,010 B1 | 2/2003 | Franchini et al. | |
| 6,558,699 B2 | 5/2003 | Venkatesh | |
| 6,627,635 B2 | 9/2003 | Palermo et al. | |
| 6,671,904 B2 | 1/2004 | Easterling | |
| 6,692,768 B1 | 2/2004 | Ishibashi et al. | |
| 6,696,088 B2 | 2/2004 | Oshlack et al. | |
| 6,699,506 B1 | 3/2004 | Paillard et al. | |
| 6,699,997 B2 | 3/2004 | Hildesheim et al. | |
| 6,761,904 B2 | 7/2004 | Bertelsen et al. | |
| 6,815,542 B2 | 11/2004 | Hong et al. | |
| 6,846,810 B2 | 1/2005 | Martin et al. | |
| 6,852,337 B2 | 2/2005 | Gabel et al. | |
| 6,903,079 B2 | 6/2005 | Jagtap et al. | |
| 6,946,146 B2 | 9/2005 | Mulye | |
| 7,022,345 B2 | 4/2006 | Valducci et al. | |
| 7,056,942 B2 | 6/2006 | Hildesheim et al. | |
| 7,126,008 B2 | 10/2006 | Hildesheim et al. | |
| 7,268,156 B2 | 9/2007 | Brook et al. | |
| 7,626,041 B2 | 12/2009 | Brook et al. | |
| 7,750,036 B2 | 7/2010 | Brook et al. | |
| 7,759,384 B2 | 7/2010 | Brook et al. | |
| 7,893,100 B2 | 2/2011 | Brook et al. | |
| 2001/0004458 A1 | 6/2001 | Opitz et al. | |
| 2001/0006650 A1 | 7/2001 | Burnside et al. | |
| 2001/0036959 A1 | 11/2001 | Gabel et al. | |
| 2001/0036960 A1 | 11/2001 | Decker et al. | |
| 2002/0052367 A1 | 5/2002 | Heller | |
| 2002/0068085 A1 | 6/2002 | Rudnic et al. | |
| 2002/0068740 A1 | 6/2002 | Mylari | |
| 2002/0099013 A1 | 7/2002 | Piccariello et al. | |
| 2002/0099046 A1 | 7/2002 | Scott | |
| 2002/0107279 A1 | 8/2002 | Barone et al. | |
| 2002/0115655 A1 | 8/2002 | Mehanna et al. | |
| 2002/0143045 A1 | 10/2002 | Hildesheim et al. | |
| 2002/0169199 A1 | 11/2002 | Gruber et al. | |
| 2002/0176888 A1 * | 11/2002 | Bartholomaeus et al. | 424/469 |
| 2002/0197327 A1 | 12/2002 | Ulrich et al. | |
| 2003/0004205 A1 | 1/2003 | Gabel et al. | |
| 2003/0004206 A1 | 1/2003 | Decker et al. | |
| 2003/0030878 A1 | 2/2003 | Jong et al. | |
| 2003/0035836 A1 | 2/2003 | Shanghvi et al. | |
| 2003/0035840 A1 * | 2/2003 | Li et al. | 424/471 |
| 2003/0036559 A1 | 2/2003 | Beyer et al. | |
| 2003/0050301 A1 | 3/2003 | Mylari | |
| 2003/0050620 A1 | 3/2003 | Odidi et al. | |
| 2003/0054041 A1 | 3/2003 | Lemmens et al. | |
| 2003/0059474 A1 | 3/2003 | Scott et al. | |
| 2003/0064108 A1 | 4/2003 | Lukas et al. | |
| 2003/0068371 A1 | 4/2003 | Oshlack et al. | |
| 2003/0068392 A1 | 4/2003 | Sackler | |
| 2003/0077297 A1 | 4/2003 | Chen et al. | |
| 2003/0083286 A1 | 5/2003 | Teng et al. | |
| 2003/0099711 A1 | 5/2003 | Meadows et al. | |
| 2003/0104052 A1 | 6/2003 | Berner et al. | |
| 2003/0104056 A1 | 6/2003 | Rudnic et al. | |
| 2003/0118641 A1 | 6/2003 | Maloney et al. | |

| | | | | | | |
|---|---|---|---|---|---|---|
| 2003/0166702 | A1 | 9/2003 | Kor et al. | EP | 0 413 120 | 2/1991 |
| 2003/0220399 | A1 | 11/2003 | Luskey et al. | EP | 0 475 536 | 3/1992 |
| 2003/0224051 | A1 | 12/2003 | Fink et al. | EP | 0 477 135 | 3/1992 |
| 2004/0010983 | A1 | 1/2004 | Eshpar | EP | 0 502 642 | 9/1992 |
| 2004/0019096 | A1 | 1/2004 | Andronis et al. | EP | 0 548 356 | 6/1993 |
| 2004/0022848 | A1 | 2/2004 | Kikuchi et al. | EP | 0 601 508 | 6/1994 |
| 2004/0022849 | A1 | 2/2004 | Castan et al. | EP | 0609961 | 8/1994 |
| 2004/0121015 | A1 | 6/2004 | Chidlaw et al. | EP | 0 624 371 | 11/1994 |
| 2004/0121676 | A1 | 6/2004 | Seko et al. | EP | 0 647 448 | 4/1995 |
| 2004/0126428 | A1 | 7/2004 | Hughes et al. | EP | 0 709 087 | 5/1996 |
| 2004/0152756 | A1 | 8/2004 | Chen et al. | EP | 0 793 959 | 9/1997 |
| 2004/0171584 | A1 | 9/2004 | Millan et al. | EP | 0 953 350 | 11/1999 |
| 2004/0175424 | A1 | 9/2004 | Castan et al. | EP | 0 953 359 | 11/1999 |
| 2004/0186158 | A1 | 9/2004 | Oh | EP | 0 968 714 | 1/2000 |
| 2004/0219208 | A1 | 11/2004 | Kawamura et al. | EP | 0 974 356 | 1/2000 |
| 2004/0219212 | A1 | 11/2004 | Castan et al. | EP | 1 062 955 | 12/2000 |
| 2004/0220250 | A1 | 11/2004 | OhBarth | EP | 1 069 896 | 1/2001 |
| 2004/0223939 | A1 | 11/2004 | Clausen et al. | EP | 1 086 694 | 3/2001 |
| 2004/0228924 | A1 | 11/2004 | Oshlack et al. | EP | 1 101 490 A1 | 5/2001 |
| 2004/0234601 | A1 | 11/2004 | Legrand et al. | EP | 1 123 700 | 8/2001 |
| 2004/0241235 | A1 | 12/2004 | Lebon et al. | EP | 1 293 209 | 3/2003 |
| 2005/0009897 | A1 | 1/2005 | Anderson et al. | FR | 2 313 915 | 1/1977 |
| 2005/0019406 | A1 | 1/2005 | Kerrish et al. | FR | 2 634 377 | 1/1990 |
| 2005/0031546 | A1 | 2/2005 | olomaus et al. | FR | 2 670 112 | 6/1992 |
| 2005/0059667 | A1 | 3/2005 | Wolff | FR | 2 725 623 | 4/1996 |
| 2005/0089572 | A1 | 4/2005 | Kumar et al. | FR | 2 759 083 | 8/1998 |
| 2005/0106249 | A1 | 5/2005 | Hwang et al. | FR | 2 811 571 | 1/2002 |
| 2005/0148779 | A1 | 7/2005 | Chen et al. | FR | 2 816 840 | 5/2002 |
| 2005/0163856 | A1 | 7/2005 | Maloney et al. | FR | 2816840 | 5/2002 |
| 2005/0169994 | A1 | 8/2005 | Burke et al. | FR | 2 830 447 | 4/2003 |
| 2005/0175695 | A1 | 8/2005 | Castan et al. | FR | 2830447 * | 4/2003 |
| 2005/0196459 | A1 | 9/2005 | Castan et al. | FR | 2 837 100 | 9/2003 |
| 2005/0214223 | A1 | 9/2005 | Bartholomaeus et al. | FR | 2 842 736 | 1/2004 |
| 2005/0266078 | A1 | 12/2005 | Jorda et al. | GB | 1 598 458 | 9/1981 |
| 2005/0281748 | A1 | 12/2005 | Hirsh et al. | GB | 2 163 747 | 3/1986 |
| 2006/0013868 | A1 | 1/2006 | Akiyama et al. | GB | 2 202 143 | 9/1988 |
| 2006/0110463 | A1 | 5/2006 | Castan et al. | JP | 5 807 3359 A | 5/1983 |
| 2006/0165807 | A1 | 7/2006 | Castan et al. | JP | 61-001613 A | 1/1986 |
| 2006/0165809 | A1 | 7/2006 | Guimberteau et al. | JP | 61-109711 A | 5/1986 |
| 2006/0182804 | A1 | 8/2006 | Burke et al. | JP | 6 303 9811 A | 2/1988 |
| 2006/0275376 | A1 | 12/2006 | Guimberteau et al. | JP | 63-301816 A | 12/1988 |
| 2007/0173464 | A1 | 7/2007 | Guimberteau et al. | JP | 02 053 721 | 2/1990 |
| 2007/0183980 | A1 | 8/2007 | Arkenau-Maric et al. | JP | 7252140 A | 10/1995 |
| 2007/0207214 | A1 | 9/2007 | Castan et al. | JP | 08 073 345 | 3/1996 |
| 2007/0238774 | A1 | 10/2007 | Brook et al. | JP | 10 509 427 | 9/1998 |
| 2007/0244182 | A1 | 10/2007 | Brook et al. | JP | 10 324 643 | 12/1998 |
| 2007/0259940 | A1 | 11/2007 | Brook et al. | JP | 11 269 064 | 10/1999 |
| 2007/0264326 | A1 | 11/2007 | Guimberteau et al. | JP | 11 322 588 | 11/1999 |
| 2008/0020018 | A1 | 1/2008 | Moodley et al. | JP | 00 256 182 | 9/2000 |
| 2008/0096951 | A1 | 4/2008 | Chen et al. | WO | WO-87/07833 | 12/1987 |
| 2008/0193540 | A1 | 8/2008 | Soula et al. | WO | WO-91/16885 | 11/1991 |
| 2008/0247959 | A1 | 10/2008 | Bartholomaus et al. | WO | WO-91/19711 | 12/1991 |
| 2008/0260844 | A1 | 10/2008 | Soula et al. | WO | WO-91/19712 | 12/1991 |
| 2008/0262069 | A1 | 10/2008 | Brook et al. | WO | WO-92/01446 | 2/1992 |
| 2009/0041838 | A1 | 2/2009 | Guimberteau et al. | WO | WO-93/01805 | 2/1993 |
| | | | | WO | WO-94/09762 | 5/1994 |

FOREIGN PATENT DOCUMENTS

| | | | | | |
|---|---|---|---|---|---|
| | | | | WO | WO-94/27557 | 12/1994 |
| CA | 2391832 | 3/2001 | | WO | WO-94/27988 | 12/1994 |
| CN | 1187121 A | 7/1998 | | WO | WO-95/20946 | 8/1995 |
| DE | 2 213 180 | 9/1972 | | WO | WO-95/28148 | 10/1995 |
| DE | 2 417 465 | 10/1975 | | WO | WO-96/01628 | 1/1996 |
| DE | 3 943 242 | 6/1990 | | WO | WO-96/04908 | 2/1996 |
| EP | 0 005 129 | 10/1979 | | WO | WO-96/08243 | 3/1996 |
| EP | 0 015 381 | 9/1980 | | WO | WO 96/11675 | 4/1996 |
| EP | 0 103 991 | 3/1984 | | WO | WO-96/39127 | 12/1996 |
| EP | 0 166 287 | 1/1986 | | WO | WO-97/06798 | 2/1997 |
| EP | 0 174 726 | 3/1986 | | WO | WO-97/21436 | 6/1997 |
| EP | 0 198 769 | 10/1986 | | WO | WO-97/25066 | 7/1997 |
| EP | 0 202 051 | 11/1986 | | WO | WO-97/40680 | 11/1997 |
| EP | 0 207 041 | 12/1986 | | WO | WO-98/02157 | 1/1998 |
| EP | 0 239 361 | 9/1987 | | WO | WO-98/10754 | 3/1998 |
| EP | 0 249 587 | 12/1987 | | WO | WO-98/24411 | 6/1998 |
| EP | 0263083 | 4/1988 | | WO | WO-98/35672 | 8/1998 |
| EP | 0 273 890 | 7/1988 | | WO | WO-98/40053 | 9/1998 |
| EP | 0 281 200 | 9/1988 | | WO | WO-98/42311 | 10/1998 |
| EP | 0 383 967 | 8/1990 | | WO | WO-98/55107 | 12/1998 |
| EP | 0 383 967 A1 | 8/1990 | | WO | WO-99/05105 | 2/1999 |
| EP | 0 391 518 | 10/1990 | | WO | WO-99/11260 | 3/1999 |
| EP | 0 411 590 | 2/1991 | | WO | WO-99/26608 | 6/1999 |

| | | |
|---|---|---|
| WO | WO-99/32091 | 7/1999 |
| WO | WO-99/47125 | 9/1999 |
| WO | WO-99/47128 | 9/1999 |
| WO | WO-99/49846 | 10/1999 |
| WO | WO-99/52526 | 10/1999 |
| WO | WO-00/00179 | 1/2000 |
| WO | WO-00/03695 | 1/2000 |
| WO | WO-00/04902 | 2/2000 |
| WO | WO-00/15639 | 3/2000 |
| WO | WO-00/18374 | 4/2000 |
| WO | WO-00/24379 | 5/2000 |
| WO | WO-00/28989 | 5/2000 |
| WO | WO-00/32174 | 6/2000 |
| WO | WO-00/40233 | 7/2000 |
| WO | WO 00/50015 | 8/2000 |
| WO | WO-00/50036 | 8/2000 |
| WO | WO-00/61115 | 10/2000 |
| WO | WO-00/78293 | 12/2000 |
| WO | WO-01/08661 | 2/2001 |
| WO | WO-01/10419 | 2/2001 |
| WO | WO-01/21159 | 3/2001 |
| WO | WO-01/32157 | 5/2001 |
| WO | WO-01/32158 | 5/2001 |
| WO | WO-01/47499 | 7/2001 |
| WO | WO-01/51035 | 7/2001 |
| WO | WO-01/51036 | 7/2001 |
| WO | WO 01/58424 | 8/2001 |
| WO | WO-01/74356 | 10/2001 |
| WO | WO-01/78725 | 10/2001 |
| WO | WO-01/87837 | 11/2001 |
| WO | WO-02/00216 | 1/2002 |
| WO | WO-02/22108 | 3/2002 |
| WO | WO-02/24167 | 3/2002 |
| WO | WO-02/30392 | 4/2002 |
| WO | WO-02/34237 | 5/2002 |
| WO | WO-02/39984 | 5/2002 |
| WO | WO-02/053097 | 7/2002 |
| WO | WO-02/056861 | 7/2002 |
| WO | WO-02/066002 | 8/2002 |
| WO | WO-02/072072 | 9/2002 |
| WO | WO-02/080887 | 10/2002 |
| WO | WO-02/092078 | 11/2002 |
| WO | WO-02/094285 | 11/2002 |
| WO | WO-03/007962 | 1/2003 |
| WO | WO-03/013467 | 2/2003 |
| WO | WO-03/013479 | 2/2003 |
| WO | WO-03/013609 | 2/2003 |
| WO | WO-03/015745 | 2/2003 |
| WO | WO-03/020243 | 3/2003 |
| WO | WO-03/024426 | 3/2003 |
| WO | WO-03/024429 | 3/2003 |
| WO | WO-03/028645 | 4/2003 |
| WO | WO-03/028718 | 4/2003 |
| WO | WO-03/030920 | 4/2003 |
| WO | WO-03/033001 | 4/2003 |
| WO | WO-03/035029 | 5/2003 |
| WO | WO-03/035039 | 5/2003 |
| WO | WO-03/077888 | 9/2003 |
| WO | WO-03/082204 | 10/2003 |
| WO | WO-03/084517 | 10/2003 |
| WO | WO-03/084518 | 10/2003 |
| WO | WO-03/092622 | 11/2003 |
| WO | WO-03/092626 | 11/2003 |
| WO | WO-03/094899 | 11/2003 |
| WO | WO-03/094924 | 11/2003 |
| WO | WO-03/097018 | 11/2003 |
| WO | WO-03/103538 | 12/2003 |
| WO | WO-2004/002419 | 1/2004 |
| WO | WO-2004/002472 | 1/2004 |
| WO | WO-2004/004693 | 1/2004 |
| WO | WO-2004/009120 | 1/2004 |
| WO | WO-2004/010983 | 2/2004 |
| WO | WO-2004/010984 | 2/2004 |
| WO | WO-2004/016249 | 2/2004 |
| WO | WO-2004/024126 | 3/2004 |
| WO | WO-2004/026262 | 4/2004 |
| WO | WO-2004/035020 | 4/2004 |
| WO | WO-2004/035090 | 4/2004 |
| WO | WO-2004/037259 | 5/2004 |
| WO | WO-2004/041252 | 5/2004 |
| WO | WO-2004/052346 | 6/2004 |
| WO | WO-2004/054542 | 7/2004 |
| WO | WO-2004/056336 | 7/2004 |
| WO | WO-2004/056337 | 7/2004 |
| WO | WO-2004/064834 | 8/2004 |
| WO | WO-2004/087175 | 10/2004 |
| WO | WO-2005/016313 | 2/2005 |
| WO | WO-2005/016314 | 2/2005 |
| WO | WO-2005/016370 | 2/2005 |
| WO | WO-2005-051322 | 6/2005 |
| WO | WO-2005/051325 | 6/2005 |
| WO | WO-2005/051383 | 6/2005 |
| WO | WO-2005/079760 | 9/2005 |
| WO | WO-2006/056712 | 6/2006 |
| WO | WO-2006/056713 | 6/2006 |
| WO | WO-2006/089843 | 8/2006 |
| WO | WO-2006/125819 | 11/2006 |
| WO | WO-2006/133733 | 12/2006 |
| WO | WO-2006/134018 | 12/2006 |
| WO | WO-2007/054378 | 5/2007 |
| WO | WO-2007/093642 | 8/2007 |

OTHER PUBLICATIONS

Yoshino, H., "Design and Evaluation of Time-Controlled Release Systems for Site-Specific Oral Drug Delivery to the GI Tract," (1993) *Current Status on Targeted Drug Delivery to the GI Tract*, Capsugel Library, Symp. Ser., Short Hills 22/04, London 6/05, Tokyo 14/05, pp. 185-190.
In the U.S. Patent and Trademark Office U.S. Appl. No. 08/544,208 Non-Final Office Action dated Feb. 11, 1999, 7 pages.
In the U.S. Patent and Trademark Office U.S. Appl. No. 08/753,013 Non-Final Office Action dated Apr. 14, 1997, 4 pages.
In the U.S. Patent and Trademark Office U.S. Appl. No. 10/332,463 Final Office Action dated Sep. 21, 2006, 10 pages.
In the U.S. Patent and Trademark Office U.S. Appl. No. 10/332,463 Non-Final Office Action dated Dec. 23, 2005, 6 pages.
In the U.S. Patent and Trademark Office U.S. Appl. No. 10/415,850 Advisory Action dated Dec. 10, 2009, 3 pages.
In the U.S. Patent and Trademark Office U.S. Appl. No. 10/415,850 Final Office Action dated Aug. 18, 2009, 8 pages.
In the U.S. Patent and Trademark Office U.S. Appl. No. 10/415,850 Final Office Action dated Nov. 23, 2010, 12 pages.
In the U.S. Patent and Trademark Office U.S. Appl. No. 10/415,850 Final Office Action dated Sep. 10, 2007, 16 pages.
In the U.S. Patent and Trademark Office U.S. Appl. No. 10/415,850 Non-Final Office Action dated Aug. 31, 2010, 4 pages.
In the U.S. Patent and Trademark Office U.S. Appl. No. 10/415,850 Non-Final Office Action dated Feb. 18, 2009, 7 pages.
In the U.S. Patent and Trademark Office U.S. Appl. No. 10/415,850 Non-Final Office Action dated Jan. 21, 2010, 11 pages.
In the U.S. Patent and Trademark Office U.S. Appl. No. 10/415,850 Non-Final Office Action dated Mar. 28, 2006, 14 pages.
In the U.S. Patent and Trademark Office U.S. Appl. No. 10/478,420 Final Office Action dated Jul. 1, 2009, 27 pages.
In the U.S. Patent and Trademark Office U.S. Patent and Trademark Office U.S. Appl. No. 10/478,420 Final Office Action dated Aug. 10, 2010, 24 pages.
In the U.S. Patent and Trademark Office U.S. Appl. No. 10/478,420 Non-Final Office Action dated Jan. 11, 2010, 29 pages.
In the U.S. Patent and Trademark Office U.S. Appl. No. 10/478,420 Non-Final Office Action dated Sep. 30, 2008, 18 pages.
In the U.S. Patent and Trademark Office U.S. Appl. No. 10/478,420 Non-Final Office Action dated Jan. 4, 2011, 6 pages.
In the U.S. Patent and Trademark Office U.S. Appl. No. 10/492,129 Non-Final Office Action dated Apr. 29, 2009, 12 pages.
In the U.S. Patent and Trademark Office U.S. Appl. No. 10/492,129 Non-Final Office Action dated Jul. 26, 2007, 9 pages.
In the U.S. Patent and Trademark Office U.S. Appl. No. 10/492,129 Non-Final Office Action dated Mar. 30, 2010, 2 pages.
In the U.S. Patent and Trademark Office U.S. Appl. No. 10/492,129 Non-Final Office Action dated Mar. 30, 2010, 9 pages.
In the U.S. Patent and Trademark Office U.S. Appl. No. 10/492,129 Non-Final Office Action dated Sep. 8, 2008, 10 pages.

In the U.S. Patent and Trademark Office U.S. Appl. No. 10/507,886 Final Office Action dated Jun. 23, 2010, 15 pages.
In the U.S. Patent and Trademark Office U.S. Appl. No. 10/507,886 Non-Final Office Action dated Jul. 21, 2009, 11 pages.
In the U.S. Patent and Trademark Office U.S. Appl. No. 10/510,621 Final Office Action dated Aug. 25, 2010, 17 pages.
In the U.S. Patent and Trademark Office U.S. Appl. No. 10/510,621 Final Office Action dated Mar. 30, 2009, 17 pages.
In the U.S. Patent and Trademark Office U.S. Appl. No. 10/510,621 Non-Final Office Action dated Dec. 8, 2009, 16 pages.
In the U.S. Patent and Trademark Office U.S. Appl. No. 10/510,621 Non-Final Office Action dated Feb. 5, 2008, 13 pages.
In the U.S. Patent and Trademark Office U.S. Appl. No. 10/510,643 Final Office Action dated Mar. 25, 2009, 19 pages.
In the U.S. Patent and Trademark Office U.S. Appl. No. 10/510,643 Non-Final Office Action dated Dec. 7, 2009, 16 pages.
In the U.S. Patent and Trademark Office U.S. Appl. No. 10/510,643 Non-Final Office Action dated Feb. 5, 2008, 14 pages.
In the U.S. Patent and Trademark Office U.S. Appl. No. 10/522,234 Non-Final Office Action dated Jan. 14, 2008, 11 pages.
In the U.S. Patent and Trademark Office U.S. Appl. No. 10/522,252 Final Office Action dated Aug. 19, 2008, 11 pages.
In the U.S. Patent and Trademark Office U.S. Appl. No. 10/522,252 Final Office Action dated Mar. 2, 2010, 9 pages.
In the U.S. Patent and Trademark Office U.S. Appl. No. 10/522,252 Non-Final Office Action dated Jan. 14, 2008, 10 pages.
In the U.S. Patent and Trademark Office U.S. Appl. No. 10/522,252 Non-Final Office Action dated Jul. 6, 2009, 12 pages.
In the U.S. Patent and Trademark Office U.S. Appl. No. 10/826,690 Final Office Action dated Jan. 7, 2009, 9 pages.
In the U.S. Patent and Trademark Office U.S. Appl. No. 10/826,690 Final Office Action dated Jul. 18, 2011, 5 pages.
In the U.S. Patent and Trademark Office U.S. Appl. No. 10/826,690 Non-Final Office Action dated Apr. 30, 2010, 8 pages.
In the U.S. Patent and Trademark Office U.S. Appl. No. 10/826,690 Non-Final Office Action dated Jul. 27, 2007, 13 pages.
In the U.S. Patent and Trademark Office U.S. Appl. No. 10/826,690 Non-Final Office Action dated Oct. 26, 2010, 11 pages.
In the U.S. Patent and Trademark Office U.S. Appl. No. 10/826,690 Non-Final Office Action dated Sep. 15, 2009, 16 pages.
In the U.S. Patent and Trademark Office U.S. Appl. No. 10/996,780 Final Office Action dated Oct. 8, 2009, 18 pages.
In the U.S. Patent and Trademark Office U.S. Appl. No. 10/996,780 Non-Final Office Action dated Dec. 12, 2008, 18 pages.
In the U.S. Patent and Trademark Office U.S. Appl. No. 10/997,836 Non-Final Office Action dated Aug. 19, 2010, 19 pages.
In the U.S. Patent and Trademark Office U.S. Appl. No. 10/997,836 Non-Final Office Action dated Aug. 7, 2009, 17 pages.
In the U.S. Patent and Trademark Office U.S. Appl. No. 10/997,836 Non-Final Office Action dated Oct. 29, 2008, 14 pages.
In the U.S. Patent and Trademark Office U.S. Appl. No. 11/137,261 Final Office Action dated Jan. 15, 2009, 23 pages.
In the U.S. Patent and Trademark Office U.S. Appl. No. 11/137,261 Non-Final Office Action dated Apr. 2, 2008, 17 pages.
In the U.S. Patent and Trademark Office U.S. Appl. No. 11/439,432 Final Office Action dated Decmeber 22, 2009, 12 pages.
In the U.S. Patent and Trademark Office U.S. Appl. No. 11/439,432 Non-Final Office Action dated Jan. 30, 2009, 22 pages.
In the U.S. Patent and Trademark Office U.S. Appl. No. 11/439,432 Non-Final Office Action dated Jul. 13, 2011, 8 pages.
In the U.S. Patent and Trademark Office U.S. Appl. No. 11/583,940 Final Office Action dated Feb. 4, 2009, 13 pages.
In the U.S. Patent and Trademark Office U.S. Appl. No. 11/583,940 Final Office Action dated May 25, 2010, 13 pages.
In the U.S. Patent and Trademark Office U.S. Appl. No. 11/583,940 Non-Final Office Action dated Mar. 3, 2008, 9 pages.
In the U.S. Patent and Trademark Office U.S. Appl. No. 11/583,940 Non-Final Office Action dated Sep. 2, 2009, 11 pages.
In the U.S. Patent and Trademark Office U.S. Appl. No. 11/648,605 Non-Final Office Action dated Apr. 15, 2009, 15 pages.
In the U.S. Patent and Trademark Office U.S. Appl. No. 11/651,577 Final Office Action dated Apr. 29, 2011, 10 pages.
In the U.S. Patent and Trademark Office U.S. Appl. No. 11/651,577 Final Office Action dated Jul. 31, 2009, 8 pages.
In the U.S. Patent and Trademark Office U.S. Appl. No. 11/651,577 Final Office Action dated Jul. 9, 2010, 8 pages.
In the U.S. Patent and Trademark Office U.S. Appl. No. 11/651,577 Non-Final Office Action dated Dec. 26, 2008, 23 pages.
In the U.S. Patent and Trademark Office U.S. Appl. No. 11/651,577 Non-Final Office Action dated Jan. 6, 2010, 7 pages.
In the U.S. Patent and Trademark Office U.S. Appl. No. 11/651,577 Non-Final Office Action dated Nov. 23, 2010, 13 pages.
In the U.S. Patent and Trademark Office U.S. Appl. No. 11/723,553 Final Office Action dated Aug. 26, 2008, 11 pages.
In the U.S. Patent and Trademark Office U.S. Appl. No. 11/723,553 Final Office Action dated Jun. 8, 2010, 20 pages.
In the U.S. Patent and Trademark Office U.S. Appl. No. 11/723,553 Non-Final Office Action dated Nov. 18, 2009, 16 pages.
In the U.S. Patent and Trademark Office U.S. Appl. No. 11/723,553 Non-Final Office Action dated Oct. 4, 2007, 7 pages.
In the U.S. Patent and Trademark Office U.S. Appl. No. 11/767,566 Final Office Action dated Dec. 18, 2008, 8 pages.
In the U.S. Patent and Trademark Office U.S. Appl. No. 11/767,566 Final Office Action dated Mar. 16, 2010, 7 pages.
In the U.S. Patent and Trademark Office U.S. Appl. No. 11/767,566 Non-Final Office Action dated Apr. 4, 2008, 11 pages.
In the U.S. Patent and Trademark Office U.S. Appl. No. 11/767,566 Non-Final Office Action dated Jul. 20, 2010, 6 pages.
In the U.S. Patent and Trademark Office U.S. Appl. No. 11/767,566 Non-Final Office Action dated Jul. 24, 2009, 8 pages.
In the U.S. Patent and Trademark Office U.S. Appl. No. 11/767,573 Final Office Action dated Dec. 10, 2008, 8 pages.
In the U.S. Patent and Trademark Office U.S. Appl. No. 11/767,573 Non-Final Office Action dated Mar. 31, 2008, 13 pages.
In the U.S. Patent and Trademark Office U.S. Appl. No. 11/767,581 Final Office Action dated Dec. 10, 2008, 8 pages.
In the U.S. Patent and Trademark Office U.S. Appl. No. 11/767,581 Final Office Action dated Nov. 26, 2008, 7 pages.
In the U.S. Patent and Trademark Office U.S. Appl. No. 11/767,581 Non-Final Office Action dated Apr. 10, 2008, 13 pages.
In the U.S. Patent and Trademark Office U.S. Appl. No. 11/767,581 Non-Final Office Action dated Jul. 29, 2009, 11 pages.
In the U.S. Patent and Trademark Office U.S. Appl. No. 11/767,581 Non-Final Office Action dated Mar. 31, 2008, 13 pages.
In the U.S. Patent and Trademark Office U.S. Appl. No. 11/767,586 Final Office Action dated Dec. 1, 2008, 7 pages.
In the U.S. Patent and Trademark Office U.S. Appl. No. 11/767,586 Non-Final Office Action dated Jul. 29, 2009, 11 pages.
In the U.S. Patent and Trademark Office U.S. Appl. No. 11/767,586 Non-Final Office Action dated Mar. 31, 2008, 13 pages.
In the U.S. Patent and Trademark Office U.S. Appl. No. 11/791,466 Final Office Action dated May 9, 2011, 8 pages.
In the U.S. Patent and Trademark Office U.S. Appl. No. 11/791,466 Non-Final Office Action dated Aug. 18, 2010, 11 pages.
In the U.S. Patent and Trademark Office U.S. Appl. No. 11/802,610 Final Office Action dated May 18, 2010, 11 pages.
In the U.S. Patent and Trademark Office U.S. Appl. No. 11/802,610 Non-Final Office Action dated Apr. 16, 2009, 9 pages.
In the U.S. Patent and Trademark Office U.S. Appl. No. 11/802,610 Non-Final Office Action dated Nov. 16, 2009, 16 pages.
In the U.S. Patent and Trademark Office, Restriction Requirement in re: U.S. Appl. No. 10/415,850, dated May 15, 2008, 6 pages.
"Product Information, Losartan (potassium salt)," *Cayman Chemical*, 2005; p. 1.
Amidon et al., "A Theoretical Basis for a Biopharmaceutic Drug Classification: The Correlation of in vitro Drug Product Dissolution and in vivo Bioavailability," *Pharmaceutical Research*, 1995; 12(3):413-420.
BASF Fine Chemicals Brochure Technical Information Cremorphor® RH 40, Aug. 1997.
Becker et al., "Current Approaches to Prevent NSAID-Induced Gastropathy—COX Selectivity and Beyond," *British Journal of Clinical Pharmacology*, 2004; 58(6):587-600.
Buri et al., "IV, Voie Orale," *Formes Pharmaceutiques Nouvelles Aspects Technologique, Biopharmaceutique et al.*, 1985; 175-227.

Catella-Lawson et al., "Cyclooxygenase Inhibitors and the Antiplatelet Effects of Aspirin," *New England Journal of Medicine*, 2001; 345(25):1809-1817.

Chou et al., "Conformational studies on copolymers of hydroxypropyl-L-glutamine and L-leucine. Circular dichroism studies," *Biochemistry*, 1972; 11(16):3028-3043.

Coloron Surelease® Aqueous Ethylcellulose Dispersions, 2007.

Corel Pharma Chem—Acrycoat Data Sheet.

Cremophor RH40 Technical Information Data Sheet.

Davis et al., "The Design and Evolution of Controlled Release Systems for the Gastrointestinal tract," *J. Controlled Release*, 1985; 2:27-38.

Evonik Industries: Eudragit® Versatile Polymers of Oral Solid Dosage Formulations. No date on document; last accessed online Aug. 11, 2011.

Evonik Industries: "Guidelines for Formulation Development and Process Technology for Protective Coatings," *Pharma Polymers*, 2009; 1-4.

Flamel Technologies, Press Release, Lyon, France, Oct. 20, 2003.

Gavrilin et al., "A Comparative Study of the Pharmacokinetics and Bioaccessibility of Potassium Losartan in Various Medicinal Forms," *Pharmaceutical Chemistry Journal*, 2002; 36(5):227-228.

Glipizide, Web search for extended release dosage information, Accessed Sep. 23, 2008, Retrieved from the Internet Archive dated Apr. 17, 2001: http://web.archive.org/web20010417064637/http://www.rxlist.com/cgi/generic/glip_ids.htm.

Hayashi, "Preparation and Properties of A-B-A Tri-Block Copolymer Membranes Consisting of N-Hydroxyalkyl L-Glutamine as the A Component and L-Alanine as the B Component," *Polymer Journal* (Tokyo, JP), 1985; 17(12):1273-1280.

Beckert et al., "Compression of enteric-coated pellets to disintegrating tablets," *International Journal of Pharmeceutics*, 1996; 143:13-23.

International Search Report from PCT/FR02/01745 dated May 23, 2002.

Jen et al., "Ribavirin dosing in chronic hepatitis C: Application of population pharmacokinetic-pharmacodynamic models," *Clin. Pharmacol. Ther.*, 2002; 72(4):349-361.

JRS Pharma: Lubritab® Brochure.

KSR v. Teleflex, Wikipedia, The Free Encyclopedia, pp. 1-3. (see Footnote 6 at p. 3, lines 14-17).

Kario et al., "Nocturnal Fall of Blood Pressure and Silent Cerebrovascular Damage in Elderly Hypertensive Patients," Advanced Silent Cerebrovascular Damage in Extreme Dippers, *Hypertension*, 1996; 27(1):130-135.

Metformin dosage information. Accessed Sep. 23, 2008, via the internet Archive dated Dec. 17, 2000, at http://web.archive.org/web/*/http://www.odist.com/cgi/generic/metformi_ids.htm.

Nicklasson et al., "Modulation of the tabletting behavior of micorcrystalline cellulose pellets by the incorporation of polyethylene glycol," *European Journal of Pharmaceutical Sciences*, 1999; 9:57-65.

Qingshseng, "Release—Sustained Pellet of Ribavirin," XP002395861, 2004 *Chemical Abstracts*, Data Accession No. 2005:353828, Abstract only.

Specifications and Test Methods of Eudragit® L100-55, 2007.

Tao et al., "Preparation of Ribavirin Sustained—Release Pellets by Centrifugal Granulation Technology," XP002395860, 2005; *Chemical Abstracts*, Database accession No. 2005:500395, Abstract only.

Torriani et al., "Peginterferon Alfa-2a plus Ribavirin for Chronic Hepatitis C Virus Infection in HIV-Infected Patients," *The New England Journal of Medicine*, 2004; 351(5):438-450.

Uchida et al., "Preparation and Evaluation of Sustained Release of Ethyl Cellulose Microcapsules Containing Ampicillin or Amoxicillin Using Rabbits, Beagle Dogs and Humans," *J. Pharmacobio-Dyn.*, 1986; 9(5):13.

Wojcik, "Helix-Coil Transition in Multicomponent Random Copolypeptides in Water. 3. Inclusion of Nearest-Neighbor Interactions and Application to Random Copolymers of (Hydroxybutyl)-$_L$-glutamine, $_L$-Alanine, $_L$-Phenylalanine, $_L$-Lysine, and Glycine," *Macromolecules*, 1990; 23(15):3655-3662.

* cited by examiner

MICROPARTICULATE ORAL GALENICAL FORM FOR THE DELAYED AND CONTROLLED RELEASE OF PHARMACEUTICAL ACTIVE PRINCIPLES

CROSS-REFERENCE TO RELATED APPLICATIONS

This application is a continuation-in-part of application Ser. No. 10/492,129, filed Jul. 19, 2004, currently pending, which is a National Stage of International Application No. PCT/FR02/03443, filed Oct. 9, 2002, which claims the benefit of FR01/12999, filed Oct. 9, 2001. International Application No. PCT/FR02/03443 and FR01/12999 are incorporated herein by reference.

The present invention relates to the field of microparticulate systems for the delayed and controlled release of one or more active principles, AP, intended for oral administration.

The AP envisaged in the present invention are those whose absorption is essentially limited to the upper parts of the gastrointestinal tract located upstream from the colon (upstream from the ileocecal junction), and which represent a large majority of pharmaceutical active principles.

More precisely, the invention relates to a microparticulate galenical form for delayed and controlled release where the controlled release phase is triggered with certainty by means of a dual mechanism: "time-dependent" release triggered after a certain residence time in the stomach, and "pH-dependent" release triggered by a change in pH when the particles enter the small intestine, which starts without a latency period. The microparticles of the present invention are microcapsules containing at least one active principle (AP)-excluding perindopril-having a particle size of between 100 and 1200 microns and individually coated with a film allowing the delayed and controlled release of the AP.

Systems for the delayed and controlled release of AP are particularly useful in cases where it is desirable, for reasons of chronobiology, that the AP be "bioabsorbed" at a precise time of day so as to be in phase with the circadian cycle. This approach is appropriate to the treatment of cancer or hypertension, the administration of anti-inflammatory drugs or the regulation of glycemia in the treatment of diabetes. It may be advantageous, for example, for the AP to be bioabsorbed very early in the morning so as to assure therapeutic cover when the patient wakes up, without compelling him to wake up prematurely. To do this, the galenical system ingested by the patient, for example after the evening meal, must allow a delayed release of the AP.

However, the first rule imposed on the pharmacist is to guarantee that the prescribed drug will be absorbed by the patient. In the case of a delayed release form, it is therefore crucial to have a total guarantee of release of the active principle at a given moment in order to obtain the therapeutic effect. Now, one is obliged to note that delayed release forms cannot ensure with certainty that the AP will be released after a prescribed time. This problem becomes particularly acute in the case where it is vital for the patient that this release does indeed take place, for example in the treatment of cardiovascular diseases or diabetes.

In fact, delayed release forms are conventionally obtained by coating the AP with a layer of enteric polymer, for example the methacrylic acid/methyl methacrylate copolymer EUDRAGIT® L. This type of enteric coating is known to have a reduced permeability under the acidic pH conditions of the stomach, and to dissolve when the pH increases to a value close to that prevailing in the small intestine, thereby releasing the AP. However, the intraindividual and interindividual variability of the gastric pH conditions and the gastric emptying time do not make it possible to ensure with certainty that the AP will be released after a given time.

Purely "time-dependent" delayed release systems, i.e. those for which the release of the AP is triggered after a given residence time in the gastrointestinal tract, are not satisfactory either. In fact, because of the intraindividual and interindividual variability of the gastric residence time, the AP may be released after it has passed its absorption window, which, for the majority of AP, is located in the upper part of the gastrointestinal tract. The bioabsorption may thus be very low or even zero.

In this context it would be particularly advantageous to have a galenical form for the delayed and controlled release of the AP which made it possible to assure with certainty the release of the AP by means of a dual AP release triggering mechanism: "time-dependent" release triggered after a controlled time m the stomach, without a change m pH, and "pH-dependent" release triggered by an increase in the pH when the galenical form enters the intestine. These two AP release triggering factors, in succession, would give the galenical system a high degree of reliability in use. The release of the AP would thus be guaranteed after a preset latency period, even if the variation in pH did not intervene as a trigger, i.e. even if the galenical form did not pass from the stomach into the intestine.

To minimize the interindividual variability of AP absorption, it is necessary to adjust the latency period preceding the release of the AP into the stomach by considering the physiological conditions of the gastrointestinal tract in man. According to the well-known results of Davis et al., J. of Controlled Release, 2, 27-38 (1985), the gastric residence time of a preparation is very variable, being in the order of 0.5 to 10 hours. It would therefore be particularly advantageous to have a galenical form which released the active principle into the stomach after a given constant latency period within this interval of 0.5-10 hours, so that the action time of the drug would be the same from one individual to another or even from one day to the next for the same individual.

Moreover, to optimize the bioavailability of AP whose absorption is mainly limited to the upper parts of the gastrointestinal tract, it would be advantageous if the "pH-dependent" release into the intestine were to take place without a latency period, since otherwise the AP would not be released in its absorption window and, consequently, the patient would not be treated.

Another unique advantage of such a system would be that, by mixing it with a galenical form for immediate release of the AP, or by mixing it with another galenical form for delayed and controlled release of the AP, it would afford release profiles which exhibited several AP release waves (one AP or several identical or different AP) or which, by appropriate adjustment of the different fractions, assured a constant plasma AP concentration level.

It would also be advantageous for the delayed and controlled release form to consist of a plurality of microcapsules with a diameter below 2000 microns. In fact, for such a form, the dose of AP to be administered is spread over a large number of microcapsules (typically 10,000 for a dose of 500 mg) and thus has the following intrinsic advantages:

The residence time of the microcapsules in the upper parts of the gastrointestinal tract can be prolonged, thereby increasing the duration of passage of the AP through the absorption windows and thus maximizing the bioavailability of the AP.

The use of a mixture of microcapsules with different delayed and controlled release profiles makes it possible to create release profiles which exhibit several release waves or which, by appropriate adjustment of the different fractions, assure a constant plasma AP concentration level.

The sensitivity to the variability of gastric emptying is reduced because the emptying, which in this case takes place over a large number of particles, is statistically more reproducible.

Bringing the tissues into contact with a high dose of AP-dose dumping-is avoided. Each microcapsule actually contains only a very small dose of AP. This eliminates the risk of tissue damage due to a local excess concentration of aggressive AP.

It is possible to combine several galenical forms (immediate and/or delayed and/or prolonged release), containing one or more active principles, in these "multimicrocapsular" systems.

It is possible to present these microcapsules in the form of sachets, gelatin capsules or tablets. In cases where the dose of AP is high (500 mg or more), the monolithic forms are too large to be swallowed easily. It is then of particular value to have a microparticulate form for delayed and controlled release of the AP, which those skilled in the art can formulate as disintegrating tablets or sachets.

Finally, it would also be desirable for the coating film around the microcapsules to be thin. In fact, a thick coating would have several adverse consequences:

(a) the mass fraction of excipient in the galenical form would be too high, making the mass of the drug too large to be swallowed easily and hence, in fine, creating compliance problems that jeopardize the success of the treatment; and (b) the microcapsules would take a very long time to manufacture.

In summary, it would therefore be of particular value to have a microparticulate oral galenical form for the delayed and controlled release of AP which simultaneously possessed the following properties:

the release of the AP can be triggered in two ways:

by release dependent on time, also called "time-dependent" release, when the residence time of the particles in the stomach exceeds 5 hours;

by release dependent on a variation in pH, also called "pH-dependent" release, which starts without a latency period when the system enters the intestine and the pH increases; these two AP release triggering factors, in succession, guarantee that the AP is released after a preset latency period, even if the variation in pH has not intervened as a trigger;

it consists of a plurality of small microcapsules of coated AP; and the mass fraction of coating excipients is limited.

The delayed or controlled release of AP has formed the subject of numerous studies.

Thus PCT patent application WO-A-96/11675 describes microcapsules for the oral administration of medicinal and/or nutritional active principles (AP) whose size is less than or equal to 1000 μm. These microcapsules consist of particles coated with a coating material consisting of a mixture of a film-forming polymeric derivative (ethyl cellulose), a hydrophobic plasticizer (castor oil), a surfactant and/or lubricant (magnesium stearate) and a nitrogen-containing polymer (polyvinylpyrrolidone: PVP). These microcapsules are also characterized by their ability to reside for a long time (at least 5 hours) in the small intestine and, during this residence time, to allow absorption of the AP over a period greater than the natural transit time in the small intestine.

The microcapsules according to said patent application do not provide a solution to the particular problem of the delayed and controlled release of AP with a "time-dependent" and "pH-dependent" triggering of the AP.

Patent application FR-A-00 14876 describes a drug for the treatment of type II diabetes which comprises several thousand antihyperglycemic microcapsules (metformin) each consisting of a core containing at least one antihyperglycemic, and of a coating film (e.g. stearic acid and ethyl cellulose) applied to the core, which allows prolonged release of the antihyperglycemic in vivo. These microcapsules have a particle size of between 50 and 1000 μm.

Said patent application FR-A-00 14876 does not indicate how to obtain the delayed 420 and controlled release of AP with a "time-dependent" and "pH-dependent" triggering of the AP.

European patent application EP-A-0 609 961 discloses oral morphine granules for which the controlled release of the AP accelerates with the increase in pH.

These granules consist of:

sugar core ($\phi$=100 to 1700 μm)

coated with a layer of active ingredient associated with a binder (PVP or hydroxypropyl methyl cellulose: HPMC), and an outer envelope based on:

a polymer that is insoluble independently of the pH (ethyl cellulose or methacrylic acid ester/ammonium methacrylate copolymer: EUDRAGIT® RS or RL), an enteric polymer that is insoluble at acidic pH (methacrylic acid/methyl methacrylate copolymer: EUDRAGIT.® L), a component that is partially soluble at acidic pH (polyethylene glycol, PVP, HPMC, polyvinyl alcohol: PVA), optionally a plasticizer (diethyl phthalate)

and optionally a filler (talcum).

The mass fractions of AP are e.g. 41%, 38% and 29% and the mass fractions of outer envelope are e.g. 14.1%, 21.5% and 12.3% (by weight).

Release of the AP takes place at any pH and increases as the pH changes from 1.2 to 7.5. This is therefore a form for prolonged and non-delayed release.

The article by H. YOSHINO entitled *"Design and evaluation of time-controlled release systems for site-specific oral drug delivery to the GI tract"*, published in *Current status on targeted drug delivery to the GI tract, Capsugel library, Symp. Ser.,* Short Hills 22/04, London 6/05, Tokyo 14/05, pp 185-190, (1993), describes multiparticulate oral galenical systems for delayed and controlled release induced by an organic acid and by the residence time in the GIT. These systems are made up of 1000 μm microcapsules consisting of a neutral sugar core coated with a layer of active ingredient mixed with an organic acid (succinic acid), and of an outer layer of methacrylic acid ester/ammonium methacrylate copolymer (EUDRAGIT®RS). The organic acid is described as allowing a rapid release of the AP after the latency phase. This organic acid is transported by the water which has entered the microcapsules through the enteric outer layer. It then works towards modifying the permeability of the coating to allow rapid diffusion of the AP out of the microcapsules. The presence of this acid in intimate contact with the AP can be detrimental to the latter.

U.S. Pat. No. 6,033,687 describes a formulation consisting of a mixture of two types of granules ($\phi$=1.4 mm) based on diltiazem, namely granules with a short latency period and granules with a long latency period. The release profiles are measured at pH 1. These granules comprise:

a neutral sugar core (φ=0.5-1.5 mm),
a layer of diltiazem associated with a binder (hydroxypropyl cellulose, carboxymethyl cellulose, ethyl cellulose, polyvinylpyrrolidone, alginate, EUDRAGIT),
and a single outer coating based on a lubricant (talcum), two methacrylic acid ester/ammonium methacrylate copolymers (EUDRAGIT®RS and EUDRAGIT®RL), a surfactant (sodium laurylsulfate) and a plasticizer (triethyl citrate).

In the granules with a short latency period, the mass fraction of the coating represents 12.3%, compared with 30.3% in the granules with a long latency period. However, this technique does not afford long latency periods for film coating rates below 30%. Furthermore, in view of the intraindividual and interindividual variability of the gastric residence time, this "time-dependent" delayed release system may release the AP after it has passed its absorption window. This results in a substantial loss of bioavailability.

Patent EP-B-0 263 083 describes a microcapsule coating composition that affords a zero-order and reproducible AP release profile. This coating composition is composed of a mixture of:

a hardening polymer to assure the mechanical strength of the coating, possible examples being ethyl cellulose or methacrylic acid copolymer(s) (EUDRAGIT®E, L, S or RS),
a lipophilic compound, e.g. stearic acid or paraffin,
and talcum.

This coating composition is present in the microcapsules in an amount of e.g. 15 to 35% by weight. The hardening polymer/lipophilic compound ratios are e.g. 44 and 42% respectively in Examples 4 and 5.

The profiles obtained are profiles without a latency period of variable duration. Said patent neither teaches nor mentions how to obtain a profile with a delayed and controlled release that is triggered at the end of the latency period and/or by a variation in pH.

Patent application WO-A-01/58424 A1 discloses "floating" microcapsules coated with an enteric coating based e.g. on EUDRAGIT®L, magnesium stearate, talcum and a plasticizer such as dibutyl sebacate. This coating can be enveloped in a "bioadhesive" film based on chitosan. Like every enteric coating, the aim of the enteric coating according to patent document WO-A-01/58424 is a "pH-dependent" release rather than the conjunction of a "time-dependent" release and a "pH-dependent" release. Furthermore, FIGS. 1 to 3 of said patent application show that the simple objective of "pH-dependent" release is very imperfectly achieved since up to 20% of the AP is released in two hours only at constant acidic pH. As the particles described in said patent application float in the stomach, their gastric residence time is described as increased, so much so that one may even fear the absence of any "pH-triggered" release. Finally, the release would take place in an uncontrolled manner due to the rogue leaks of AP into the stomach.

European patent application EP-A-1 101 490 relates to a pharmaceutical preparation that is capable of releasing an active principle into the large intestine and more particularly the colon. This preparation can consist of tablets or granules comprising a core and a coating.

The technical problem underlying said invention is to propose a pharmaceutical form that is capable of allowing the release of a medicinal substance at a target site in the lower part of the small intestine, the ascending colon, the transverse colon or the lower part of the large intestine. Given the fact that the mean residence time in the stomach is 5 hours and that, on average, a further 2 hours are required to reach the lower part of the small intestine, the preparation according to EP-A-1 101 490 is designed so that the medicinal substance is not released for 5 hours under acidic conditions simulating the stomach, and is only released after a latency period of at least 2 hours in a fluid simulating the pH conditions of the intestine (cf. especially claim 7 of EP-A-1 101 490).

It is therefore apparent that this system aimed at medicinal substances absorbed in the lower parts of the intestine (colon) is not suitable for medicinal substances mainly absorbed in the upper parts of the gastrointestinal tract. Moreover, the system according to European patent application EP-A-1 101 490 does not make provision for release of the AP by means of a dual release triggering mechanism:

release into the stomach after a constant given latency period within an interval of 0.5-10 hours ("time-dependent" mechanism),
and release without a latency period after entering the intestine ("pH-dependent" mechanism).

Finally, the problem of the interindividual or intraindividual variability of the gastric residence time is not solved by the preparation according to EP-A-1 101 490.

Thus the prior art does not comprise a galenical system that makes it possible to delay and to guarantee with certainty the release of AP preferentially absorbed in the upper parts of the gastrointestinal tract, by means of a dual release mechanism:

"time-dependent" release after a latency period in the stomach which has the characteristic of being a constant given latency period within an interval of 0.5-10 hours, and "pH-dependent" release without a latency period.

In view of this state of the art, one of the essential objectives of the present invention is to provide a novel multimicroparticulate galenical system for the oral administration of active principles essentially absorbed in the upper parts of the gastrointestinal tract, this system being of the delayed and controlled release type that assures the release of the AP with certainty and hence guarantees the therapeutic efficacy of said system, by means of a dual "time-dependent" and "pH-dependent" release mechanism. These two AP release triggering factors, in succession, guarantee the release of the AP after a preset latency period, even if the variation in pH has not intervened as a trigger.

One essential objective of the present invention is to propose a galenical form made up of a plurality of microcapsules that makes it possible to escape from the interindividual and intraindividual variability of the gastric emptying time by releasing the AP at pH 1.4 according to a delayed release profile which has a latency period with an adjustable given duration of between 0.5 and 10 hours, followed by a release phase that starts without a latency period.

One essential objective of the present invention is to propose a galenical form made up of a plurality of microcapsules that makes it possible on the one hand to release the AP according to a delayed release profile at pH 1.4 with a constant given latency period of between 0.5 and 10 hours, and according to a release half-life $t_{1/2}$ of between 0.25 and 35 hours, and on the other hand to release the AP when the pH changes from 1.4 to 6.8, without a latency period and with a $t_{1/2}$ of between 0.25 and 20 hours.

One essential objective of the present invention is controlled when the pH changes from 1.4 to 6.8.

One objective of the present invention is to propose a galenical form consisting of a large number of microcapsules, for example in the order of several thousand, this multiplicity statistically assuring a good reproducibility of the AP transit kinetics throughout the gastrointestinal tract, the result being a better control of the bioavailability and hence a better efficacy.

One essential objective of the present invention is to propose a galenical form made up of a plurality of coated microcapsules that avoids the use of large amounts of coating agent, the mass fraction of coating agent being comparable to that of monolithic forms.

One essential objective of the present invention is to propose a pharmaceutical form made up of a plurality of coated microcapsules that makes it possible to present the AP in a form that is easy to swallow, namely a sachet or a disintegrating tablet.

One essential objective of the present invention is to propose a pharmaceutical form made up of a plurality of coated microcapsules that makes it possible to mix several different active principles.

Another objective of the present invention is to propose a pharmaceutical form made up of a plurality of coated microcapsules each containing a neutral core.

Having set themselves the above objectives, among others, it was to the inventors' credit to have developed, in order to assure a certain release of AP mainly absorbed in the upper parts of the gastrointestinal tract and a good bioabsorption of pharmaceutical active principles, a multimicrocapsular galenical system which:
  guarantees the absorption of the AP in its absorption window, which is mainly limited to the upper parts of the gastrointestinal tract;
  thereby assures a certain therapeutic efficacy of this system or of this galenical form;
  and has the essential characteristic of a dual triggering of the AP release.

This represents a major advance compared with the AP controlled release systems known hitherto, in which the release of the AP is triggered by a single factor, namely the residence time in the gastrointestinal tract for some systems and a variation in pH for other systems.

Thus the invention, which satisfies the objectives laid out above, among others, relates to a microparticulate oral galenical form for the delayed and control release of at least one AP-excluding perindopril-this AP having an absorption window in vivo that is essentially limited to the upper parts of the gastrointestinal tract, said form being designed so as to guarantee its therapeutic efficacy by guaranteeing its absorption in vivo, and being characterized in that:
  the release of the AP is governed by two different triggering mechanisms, one being based on a variation in pH and the other allowing the release of the AP after a predetermined residence time in the stomach,
  and its dissolution behavior in vitro (determined as indicated in the European Pharmacopeia, 3rd edition, under the title: "Dissolution test for solid oral forms": type II dissolutest performed under SINK conditions, maintained at 37° C. and agitated at 100 rpm) is such that:
    at a constant pH of 1.4, the dissolution profile includes a latency phase with a duration less than or equal to 5 hours, preferably of between 1 and 5 hours,
    and the change from pH 1.4 to pH 6.8, during the latency phase, results in a release phase that starts without a latency period.

In one preferred embodiment of the invention, the microparticulate oral galenical form consists of a plurality of microcapsules containing at least one active principle (AP) mainly absorbed in the upper parts of the gastrointestinal tract-excluding perindopril-these microcapsules being of the type that:
  consist of particles of AP each coated with at least one film, this coating film consisting of a composite material which:
    comprises:
      at least one hydrophilic polymer A carrying groups that are ionized at neutral pH,
      and at least one hydrophobic compound B;
    and represents a mass fraction (% by weight, based on the total mass of the microcapsules) of $\leq 40$;
  and have a diameter below 2000 microns, preferably of between 200 and 800 microns and particularly preferably of between 200 and 600 microns,
characterized in that their coating film consists of a composite based on A and B in which:
  the weight ratio B/A is between 0.45 and 1.0, preferably between 0.5 and 1,
  and the hydrophobic compound B is selected from products that are crystalline in the solid state and have a melting point $T_{fB}$ such that, $T_{fB} \geq 40°$ C., preferably $T_{fB} \geq 50°$ C.

Advantageously, the microcapsules have a diameter of between 200 and 800 microns, B/A is between 0.5 and 1.0 and the hydrophobic compound B is selected from products that one cristalline in the solid state and have a melting point $T_{FB}$ such that $40°$ C.$\leq T_{FB} \leq 90°$ C.

According to one preferred characteristic of the invention, the hydrophilic polymer A is selected from:
  (meth)acrylic acid/alkyl (e.g. methyl) (meth)acrylate copolymers (EUDRAGIT®S or L) and mixtures thereof;
  cellulose derivatives, preferably cellulose acetate and/or phthalate, hydroxypropyl methyl cellulose phthalate and hydroxypropyl methyl cellulose acetate and/or succinate;
  and mixtures thereof.

More preferably, the compound B is selected from the following group of products:
  vegetable waxes, taken on their own or in mixtures with one another;
  hydrogenated vegetable oils, taken on their own or in a mixture with one another;
  mixtures of at least one monoester and of at least one diester and/or of at least one triester of glycerol with at least one fatty acid;
  and mixtures thereof.

According to the most preferred embodiment of the instant invention, the compound B of the microcapsules' coating film is selected from the groups comprising: the products which tradenames (trademarks) are the followings: Dynasan (Hydrogenated palm oil), Cutina (Hydrogenated castor oil), Hydrobase (Hydrogenated soybean oil), Dub (Hydrogenated soybean oil), Castorwax (Hydrogenated castor oil), Croduret (Hydrogenated castor oil), Carbowax, Compritol (Glyceryl behenate), Sterotex (Hydrogenated cottonseed oil), Lubritab (Hydrogenated cottonseed oil), Apifil (Wax yellow), Akofine (Hydrogenated cottonseed oil), Softtisan (Hydrogenated palm oil), Hydrocote (Hydrogenated soybean oil), Livopol (Hydrogenated soybean oil), Super Hartolan (Lanolin), MGLA (Anhydrous milk fat), Corona (Lanolin), Protalan (Lanolin), Akosoft (Suppository bases, Hard fat), Akosol (Suppository bases, Hard fat), Cremao (Suppository bases, Hard fat), Massupol (Suppository bases, Hard fat), Novata (Suppository bases, Hard fat), Suppocire (Suppository bases, Hard fat), Wecobee (Suppository bases, Hard fat), Witepsol (Suppository bases, Hard fat), Coronet, Lanol, Lanolin, Incromega (Omega 3), Estaram (Suppository bases, Hard fat), Estol, Suppoweiss (Suppository bases, Hard fat), Gelucire (Macrogolglycérides Lauriques), Precirol (Glyceryl Palmitostearate), Emulcire (Cetyl alcohol), Plurol diisostearique (Polyglyceryl Diisostearate), Geleol (Glyceryl Stearate), Hydrine et Monthyle; as well the additives which codes are the followings: E 901, E 907, E 903 and mixtures thereof; and mixtures thereof.

In practice, the compound can be selected from the group comprising the products which tradenames (trademarks) are the followings: Dynasan P60, Dynasan 116, Dynasan 118, Cutina HR, Hydrobase 66-68, Dub, Compritol 888, Sterotex NF, Lubritab and mixtures thereof.

According to an interesting embodiment of the invention, the coating film of the 120 microcapsules is free from talc.

The preferred polymers A are (meth)acrylic acid/alkyl (e.g. methyl) (meth)acrylate copolymers. These copolymers, which are e.g. of the type marketed by RÖHM PHARMA POLYMERS under the registered trade marks EUDRAGIT®L and S series (for example EUDRAGIT® L100, S100, L30D-55 and L100-55), are anionic enteric (co) polymers soluble in aqueous media at pH values above those encountered in the stomach.

According to another preferred characteristic of the invention, the compound B is selected from the following group of products:
vegetable waxes, taken on their own or in mixtures with one another, such as those marketed under the marks DYNASAN® P60 and DYNASAN® 116, inter alia;
hydrogenated vegetable oils, taken on their own or in a mixture with one another, preferably selected from the group comprising hydrogenated cottonseed oil, hydrogenated soybean oil, hydrogenated palm oil and mixtures thereof;
monoesters and/or diesters and/or triesters of glycerol with at least one fatty acid, preferably behenic acid, taken by themselves or in a mixture with one another;
and mixtures thereof.

The AP release triggering mechanism without a variation in pH, after a predetermined residence time in the stomach, results especially from control of the hydration rate of the microcapsules and/or the dissolution rate of one or more components of the microcapsules. For example, and without implying a limitation, the hydration of the microcapsule can be controlled by:
the presence, in the microcapsules, of hydrophilic products that make it possible to adjust the osmotic pressure or to cause a swelling of the microcapsules;
regulation of the water permeability of the coating film;
the creation of a microporosity in the coating film;
or even the hydration or dissolution of a compound in the coating film.

One of the decisive advantages of the multimicrocapsular galenical system according to the invention for the delayed and controlled release of AP is that it involves, in vivo, two factors that trigger the release of the AP into the gastrointestinal tract, namely:
the residence time in the stomach: "time-triggered" release,
and the variation in pH: "pH-triggered" release.

These two AP release triggering factors are successive, so they give the galenical system a high degree of reliability in use. The release of the AP is thus guaranteed after a preset latency period, even if the variation in pH has not intervened as a trigger. The problems of interindividual variability are thus overcome. The therapeutic efficacy of the drug comprising such a galenical system is assured by observing a predetermined chronobiology adapted to the intended therapeutic performance.

In addition, in the case of the AP considered in the present invention whose absorption window is limited to the upper parts of the gastrointestinal tract, it is particularly advantageous if the form for delayed and then controlled release consists of a plurality of microcapsules. In fact, for such a form, the dose of AP to be administered is spread over a large number of microcapsules (typically 10,000 for a dose of 500 mg) and thus has the following intrinsic advantages:
The residence time of the microcapsules in the upper parts of the gastrointestinal tract can be prolonged, thereby increasing the duration of passage of the AP through the absorption windows and thus maximizing the bioavailability of the AP.
The use of a mixture of microcapsules with different delayed and controlled release profiles makes it possible to create release profiles which exhibit several release waves or which, by appropriate adjustment of the different fractions, assure a constant plasma AP concentration level.
The variability of the gastric emptying is reduced because the emptying, which in this case takes place over a large number of particles, is statistically more reproducible.
Bringing the tissues into contact with a high dose of AP-dose dumping-is avoided. Each microcapsule actually contains only a very small dose of AP. This eliminates the risk of tissue damage due to a local excess concentration of aggressive AP.
It is possible to present these microcapsules in the form of sachets, gelatin capsules or tablets. In cases where the dose of AP is high (500 mg or more), the monolithic forms are too large to be swallowed easily. It is then of particular value to have a microparticulate form for delayed and controlled release of the AP, which those skilled in the art can formulate as disintegrating tablets or sachets.

The multimicrocapsular galenical system according to the invention makes it possible to assure with certainty a delayed and controlled release of the AP into the GIT by means of two triggers, and thus to escape the interindividual and interindividual variability of the gastric emptying conditions, while at the same time being economically viable and easy to ingest (optimized compliance).

According to one particularly advantageous characteristic of the preferred embodiment, at a constant pH of 1.4, the controlled release phase following the latency phase is such that the release time for 50% by weight of the AP ($t_{1/2}$) is defined as follows (in hours):

| | |
|---|---|
| | $0.25 \leq t_{1/2} \leq 35$ |
| preferably | $0.5 \leq t_{1/2} \leq 20$ |

In practice, the release phase of the in vitro AP release profile at a constant pH of 1.4 has an adjustable release half-life.

According to another valuable characteristic of the preferred embodiment, the release phase following the change from pH 1.4 to pH 6.8, which takes place without a latency period, is such that the release time for 50% of the AP ($t_{1/2}$) is defined as follows (in hours):

| | |
|---|---|
| | $0.25 \leq t_{1/2} \leq 20$ |
| preferably | $0.5 \leq t_{1/2} \leq 15$ |

Preferably, the microcapsules according to the invention comprise a single composite coating film AB. This simplifies their preparation and limits the coating rate.

Preferably, the AP is deposited on a neutral core with a diameter of between 200 and 800 microns, preferably of between 200 and 600 microns.

Without implying a limitation, the hydrophilic neutral core can contain sucrose and/or dextrose and/or lactose, or it can consist of a cellulose microsphere.

Advantageously, the microcapsule coating can comprise, in addition to the essential constituents A and B, other conventional ingredients known to those skilled in the art, such as especially:

colorants;

plasticizers, for example dibutyl sebacate;

hydrophilic compounds, for example cellulose and derivatives thereof or polyvinylpyrrolidone and derivatives thereof;

and mixtures thereof.

Advantageously, the AP is deposited by the techniques known to those skilled in the art, for example the technique of spray coating in a fluidized air bed onto neutral cores with a diameter of between 200 and 800 microns, preferably of between 200 and 600 microns.

From the quantitative point of view, the monolayer of coating agent represents at most 40% and preferably at most 30% by weight of the microcapsules. Such a limited coating rate makes it possible to produce galenical units each containing a high dose of active principle without exceeding a prohibitive size as regards swallowing. This can only improve compliance with the treatment and hence its success.

In qualitative terms, the AP of the microcapsules according to the invention is essentially absorbable in the upper parts of the gastrointestinal tract and is advantageously selected from one of the following families of active substances: antiulcer agents, antidiabetics, anticoagulants, antithrombics, hypolipidemics, antiarrhythmics, vasodilators, antiangina agents, antihypertensives, vasoprotectors, fertility promoters, labor inducers and inhibitors, contraceptives, antibiotics, antifungals, antivirals, anticancer agents, anti-inflammatories, analgesics, antiepileptics, antiparkinsonian agents, neuroleptics, hypnotics, anxiolytics, psychostimulants, antimigraine agents, antidepressants, antitussives, antihistamines and anti-allergics.

Reference may also be made to the list of active principles given on pages 4 to 8 of patent application EP-A-0 609 961.

Preferably, the AP is selected from the following compounds: metformin, acetylsalicylic acid, amoxicillin, pentoxifyllin, prazosin, acyclovir, nifedipine, diltiazem, naproxen, ibuprofen, flurbiprofen, ketoprofen, fenoprofen, indomethacin, diclofenac, fentiazac, estradiol valerate, metoprolol, sulpiride, captopril, cimetidine, zidovudine, nicardipine, terfenadine, atenolol, salbutamol, carbamazepine, ranitidine, enalapril, simvastatin, fluoxetine, alprazolam, famotidine, ganciclovir, famciclovir, spironolactone, 5-asa, quinidine, morphine, pentazocine, paracetamol, omeprazole, metoclopramide and mixtures thereof.

The microparticulate oral galenical form according to the invention can be a form selected in the groups comprising a tablet (advantageously a tablet that disperses in the mouth), a powder or a gelatin capsule.

The microcapsules described above can be used for the manufacture of novel pharmaceutical or dietetic preparations of various AP which have optimized therapeutic or dietetic performance characteristics and are preferably presented in the form of tablets, advantageously disintegrating tablets and even more preferably tablets that disperse in the mouth, powders or gelatin capsules.

These microcapsules are all the more valuable because they are also perfectly tolerated by the organism, especially by the stomach, and furthermore can be obtained easily and economically.

The present invention further relates to these novel pharmaceutical or dietetic preparations as such, which are original in their structure, to their presentation and to their composition. Such pharmaceutical or dietetic preparations are administered orally, preferably as single daily doses.

It is pointed out that it may be of value to mix, in one and the same gelatin capsule, tablet or powder, at least two types of microcapsule whose release kinetics are different but within the framework characteristic of the invention.

It is also possible to mix the microcapsules according to the invention with a certain amount of AP that is immediately available in the organism.

It can also be envisaged to associate microcapsules containing different AP.

In addition, a further subject of the invention is a galenical (pharmaceutical or dietetic) system, preferably in the form of a tablet, advantageously a disintegrating tablet and even more preferably a tablet that disperses in the mouth, a powder or a gelatin capsule, characterized in that it comprises microcapsules such as described above.

Furthermore, the invention relates to the use of microparticles such as defined above for the preparation of microparticulate oral galenical (pharmaceutical or dietetic) forms, preferably as tablets, advantageously tablets that disperse in the mouth, powders or gelatin capsules.

Finally, the invention further relates to a method of therapeutic treatment, characterized in that it consists in ingesting, according to a given dosage, a drug comprising microcapsules such as defined above.

The invention will be explained more clearly by the Examples below, given solely by way of illustration, which afford a good understanding of the invention and show its variants and/or modes of implementation, as well as its different advantages.

EXAMPLES

EXAMPLES

Example 1

Preparation of microcapsules allowing a dual-mechanism delayed and prolonged release of metformin.HCl 75 g of metformin.HCl (Chemsource) and 75 g of PVP are dissolved in 1350 g of isopropanol. The solution is sprayed onto 850 g of neutral microspheres (NP Pharm) in a Glatt® GPCG3 spray coater.

93.3 g of hydrogenated palm oil (Hüls) (B) and 140 g of Eudragit® L100 (Röhm) (A) are dissolved in hot isopropanol. B/A=0.66. The solution is sprayed onto 700 g of previously prepared microparticles. The film coating conditions are: inlet temperature: 45° C., spraying rate: 8-12 g/min, atomization pressure: 1.5 bar.

The microcapsules were tested in a type II dissolutest according to the Pharmacopeia, at 37° C. and with agitation at 100 rpm, in the following media:
 a) HCl at pH 1.4
 b) HCl at pH 1.4 for 3 hours, then $KH_2PO_4$/NaOH buffer medium at pH 6.8

Figure 1:
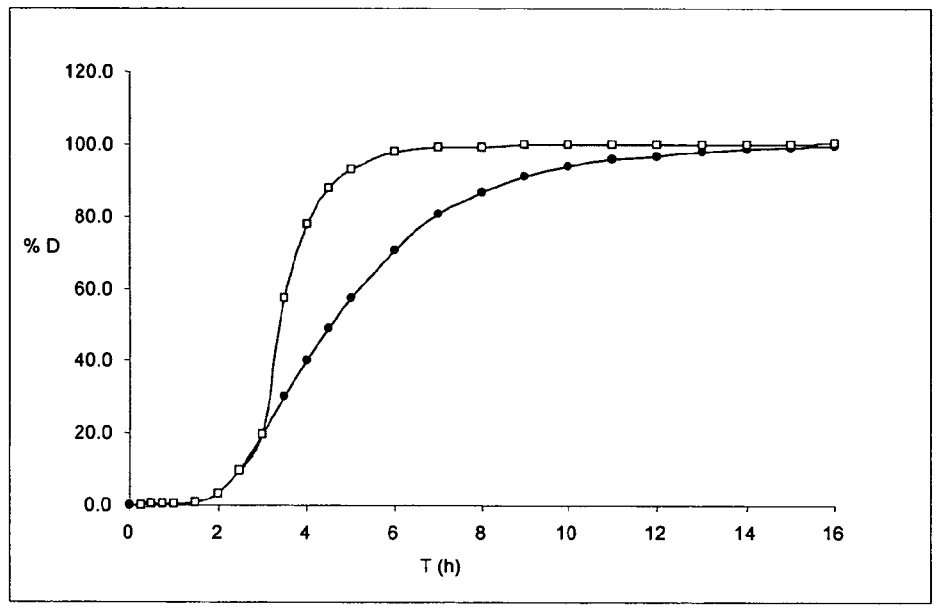
FIG. 1 shows the in vitro release profiles of the microcapsules of Example 1 at pH 1.4 —•—, and at pH 1.4 for 3 hours and then at pH 6.8 as from T=3 hours: —□—, in % by weight (% D) of dissolved metformin as a function of the time T in hours.

The release profiles are shown in FIG. 1.

These profiles are characteristic of a delayed and then prolonged release by means of a dual mechanism: absence of release for 2 hours, followed by a prolonged release without a change in pH, and finally followed by a release accelerated by the change in pH.

Example 2

Preparation of microcapsules allowing a dual-mechanism delayed and prolonged release of acyclovir 75 g of acyclovir and 75 g of the polyvinylpyrrolidone PLASDONE® K29/32 are dissolved in 833 g of isopropanol. The solution is sprayed onto 850 g of neutral microspheres (NP Pharm) in a Glatt® GPCG3 spray coater.

93.3 g of hydrogenated palm oil (Hüls) (B) and 140 g of EUDRAGIT®L100 (Röhm) (A) are dissolved in hot isopropanol. B/A=0.66. The solution is sprayed onto 700 g of previously prepared microparticles. The film coating conditions are: inlet temperature: 45° C., spraying rate: 8-12 g/min, atomization pressure: 1.5 bar.

The microcapsules were tested in a type II dissolutest according to the Pharmacopeia, at 37° C. and with agitation at 100 rpm, in the following media:
 c) HCl at pH 1.4
 d) HCl at pH 1.4 for 3 hours, then $KH_2PO_4$/NaOH buffer medium at pH 6.8

Figure 2:
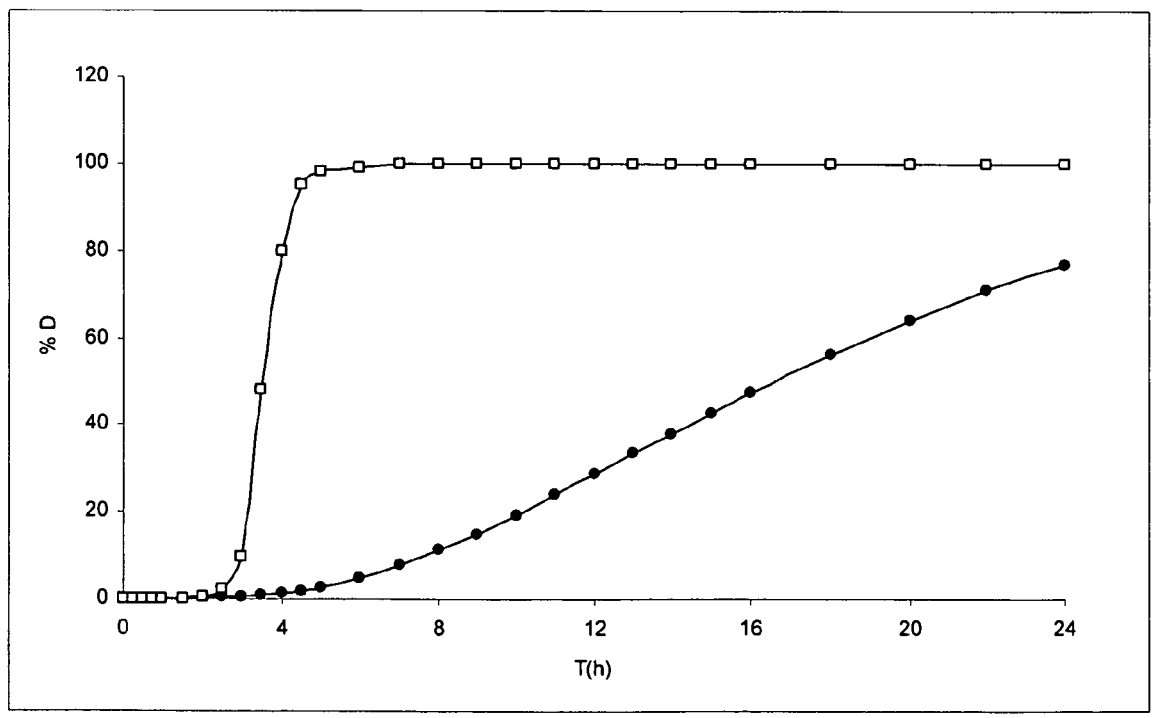
FIG. 2 shows the in vitro release profiles of the microcapsules of Example 2 at pH 1.4: —•—, and at pH 1.4 for 2 hours and then at pH 6.8 as from 2 hours: —□—, in % by weight (% D) of acyclovir as a function of the time T in hours.

The release profiles are shown in FIG. 2.

The acyclovir release profile obtained at pH 1.4 is characteristic of a delayed and prolonged release by means of a dual release triggering mechanism.

Example 3

Preparation of microcapsules allowing a dual-mechanism delayed and prolonged release of metformin.HCl 105 g of hydrogenated palm oil (Hüls) (B), 30 g of dibutyl sebacate and 165 g of Eudragit®L100 (Röhm) (A) are dissolved in hot isopropanol. B/A=64. The solution is sprayed onto 700 g of metformin granules (95.5% metformin/4.5% PVP). The film coating conditions are: inlet temperature: 45° C., spraying rate: 8-12 g/min, atomization pressure: 1.5 bar.

The microcapsules were tested in a type II dissolutest according to the Pharmacopeia, at 37° C. and with agitation at 100 rpm, in the following media:
 e) HCl at pH 1.4
 f) $KH_2PO_4$/NaOH buffer medium at pH 6.8

Figure 3:
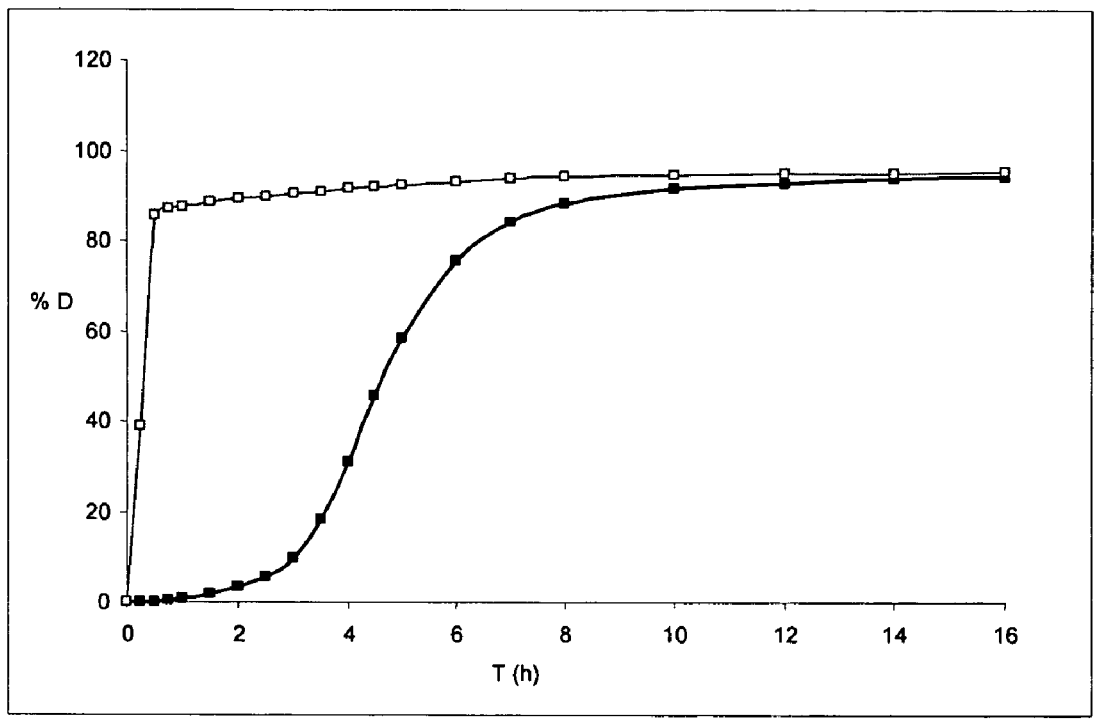
FIG. 3 shows the in vitro release profiles of the microcapsules of Example 3 at pH 1.4: —■— and at pH 6.8: —□—, in % by weight (% D) of metformin as a function of the time T in hours.

The release profiles are shown in FIG. 3.

These profiles are characteristic of a delayed and then prolonged release by means of a dual mechanism: absence of release for 2 hours at acidic pH and rapid release at neutral pH.

The invention claimed is:

1. Microparticulate oral pharmaceutical dosage form for the delayed and controlled release of at least one active principle (AP)—excluding perindopril—this active principle having an absorption window in vivo that is essentially limited to the upper parts of the gastrointestinal tract,
 wherein the dosage form comprises "reservoir" microcapsules of active principle, each coated with one single, composite coating film,
 wherein the single, composite coating film comprises at least one hydrophilic polymer A carrying groups that are ionized at neutral pH, and at least one hydrophobic compound B;
 wherein the at least one hydrophobic compound B is selected from the group consisting of hydrogenated vegetable oils, vegetable waxes, wax yellow, wax white, wax microcrystalline, lanolin, anhydrous milk fat, hard fat suppository base, lauroyl macrogolglycerides, cetyl alcohol, polyglyceryl diisostearate, diester or triester of glycerol with at least one fatty acid and mixtures thereof;
 wherein the microcapsules have a diameter of between 200 and 800 microns;
 wherein the weight ratio B/A is between 0.5 and 1.5;
 wherein the release of the active principle is governed by two different triggering mechanisms,
 wherein the first triggering mechanism releases the at least one active principle based on a variation in pH,
 wherein the second triggering mechanism releases the at least one active principle after a predetermined residence time in the stomach,
 wherein the dissolution behavior of the pharmaceutical dosage in vitro is such that:
  at a constant pH of 1.4, the dissolution profile includes a latency phase with a duration less than or equal to 5 hours, and a controlled release phase following the latency phase such that the release time for 50% of the active principle ($t_{1/2}$) is between 0.5 hour and 35 hours, and
  the change from pH 1.4 to pH 6.8 results in a release phase that starts without a latency period.

2. The pharmaceutical dosage form according to claim 1, wherein the dissolution profile includes a latency phase with a duration of between 1 and 5 hours.

3. The pharmaceutical dosage form according to claim 1, wherein the mass fraction of the coating film (% by weight, based on the total mass of the microcapsules) is less than or equal to 40.

4. The pharmaceutical dosage form according to claim 1, wherein the weight ratio B/A is between 0.5 and 1.0.

5. The pharmaceutical dosage form according to claim 1, wherein the at least one hydrophilic polymer A is selected from the group consisting of: (meth)acrylic acid polymers, alkyl (meth)acrylate polymers, (meth)acrylic acid/alkyl (meth)acrylate copolymers, cellulose derivatives, cellulose acetate phthalate, hydroxypropyl methyl cellulose phthalate, hydroxypropyl methyl cellulose acetate succinate; and mixtures thereof 6. The pharmaceutical dosage form according to claim 1, wherein the at least one hydrophilic polymer A is selected from the group consisting of: (meth)acrylic acid/ methyl (meth)acrylate copolymers, cellulose acetate phthalate, hydroxypropyl methyl cellulose phthalate, hydroxypropyl methyl cellulose acetate succinate; and mixtures thereof 7. The pharmaceutical dosage form according to claim 1, wherein said hydrophobic compound B is selected from the group consisting of: hydrogenated cottonseed oil, hydrogenated soybean oil, hydrogenated palm oil, glyceryl behenate, hydrogenated castor oil, Carnauba wax, tristearin, tripalmitin, trimyristin, glyceryl palmitostearate, and any mixtures thereof.

8. The pharmaceutical dosage form according to claim 7, wherein said hydrophobic compound B is selected from the group consisting of: hydrogenated cottonseed oil, hydrogenated soybean oil, hydrogenated palm oil, glyceryl behenate, hydrogenated castor oil, tristearin, tripalmitin, trimyristin and any mixtures thereof.

9. The pharmaceutical dosage form according to claim 1 wherein the coating film of the microcapsules is free from talc.

10. The pharmaceutical dosage form according to claim 1, characterized in that the release phase following the change from pH 1.4 to pH 6.8, which takes place without a latency period, is such that the release time for 50% of the active principle ($t_{1/2}$) is defined as follows (in hours): $0.5 \leq t_{1/2} \leq 20$.

11. The pharmaceutical dosage form according to claim 1, wherein the active principle is deposited on a neutral core with a diameter of between 200 and 600 microns.

12. The pharmaceutical dosage form according to claim 11, wherein the neutral core contains sucrose or dextrose or lactose.

13. The pharmaceutical dosage form according to claim 11, wherein the neutral core is a cellulose microsphere.

14. The pharmaceutical dosage form according to claim 1, wherein the at least one active principle is selected from the group consisting of: antiulcer agents, antidiabetics, anticoagulants, antithrombics, hypolipidemics, antiarrhythmics, vasodilators, antiangina agents, antihypertensives, vasoprotectors, fertility promoters, labor inducers and inhibitors, contraceptives, antibiotics, antifungals, antivirals, anticancer agents, anti-inflammatories, analgesics, antiepileptics, antiparkinsonian agents, neuroleptics, hypnotics, anxiolytics, psychostimulants, antimigraine agents, antidepressants, antitussives, antihistamines and antiallergics.

15. The pharmaceutical dosage form according to claim 14, wherein the active principle is selected from the group consisting of amoxicillin, metformin, acetylsalicylic acid, pentoxifyllin, prazosin, acyclovir, nifedipine, diltiazem, naproxen, ibuprofen, flurbiprofen, ketoprofen, fenoprofen, indomethacin, diclofenac, fentiazac, estradiol valerate, metoprolol, sulpiride, captopril, cimetidine, zidovudine, nicardipine, terfenadine, atenolol, salbutamol, carbamazepine, ranitidine, enalapril, simvastatin, fluoxetine, alprazolam, famotidine, ganciclovir, famciclovir, spironolactone, 5-asa, quinidine, morphine, pentazocine, paracetamol, omeprazole, metoclopramide and mixtures thereof 16. The pharmaceutical dosage form according to claim 1, wherein said pharmaceutical dosage form is selected from the group consisting of: a tablet, a powder and a capsule.

17. The pharmaceutical dosage form according to claim 1 which is a tablet that disperses in the mouth.

* * * * *